(12) United States Patent
Siekas et al.

(10) Patent No.: US 7,094,222 B1
(45) Date of Patent: Aug. 22, 2006

(54) SYRINGE DEVICE FOR SIMULTANEOUS INFUSION AND WITHDRAWAL

(75) Inventors: Jeremy John Siekas, Portland, OR (US); Deborah Valerie Pence, Corvallis, OR (US); James Anthony Liburdy, Philomath, OR (US)

(73) Assignee: The United States of America as represented by the Secretary of Navy, Washington, DC (US)

( * ) Notice: Subject to any disclaimer, the term of this patent is extended or adjusted under 35 U.S.C. 154(b) by 502 days.

(21) Appl. No.: 10/425,790

(22) Filed: Apr. 28, 2003

(51) Int. Cl.
*A61M 5/00* (2006.01)
(52) U.S. Cl. .................................................. 604/191
(58) Field of Classification Search .................. 604/6, 604/12, 110, 181, 183, 184, 187, 191, 194; 128/DIG. 1
See application file for complete search history.

(56) References Cited

U.S. PATENT DOCUMENTS

| | | | |
|---|---|---|---|
| 4,150,669 A | | 4/1979 | Latorre |
| 4,578,064 A | * | 3/1986 | Sarnoff et al. ............... 604/191 |
| 5,389,076 A | * | 2/1995 | Shaw ........................ 604/110 |
| 6,065,371 A | | 5/2000 | Yacowitz |
| 6,245,046 B1 | * | 6/2001 | Sibbitt ........................ 604/191 |
| 6,332,875 B1 | | 12/2001 | Inkpen |

\* cited by examiner

*Primary Examiner*—Nicholas D. Lucchesi
*Assistant Examiner*—Matthew F. DeSanto
(74) *Attorney, Agent, or Firm*—Peter A. Lipovsky; Michael A. Kagan; Allan Y. Lee

(57) ABSTRACT

A syringe device includes a first chamber defined by a cylindrical barrel, a plunger head within the barrel and a hollow needle sealed to an administering end of the barrel but open to an environment outside of the first chamber. A second chamber is defined by the barrel, the plunger head and a seal that seals around a plunger shaft leading to the plunger head and that seals an actuation end of the barrel. A receiving container having a second hollow needle attached and sealed at one end is also attached and sealed to the syringe, to thereby define a receiving chamber in fluid communication with the second chamber of the syringe and, via the second needle, with an environment outside of the receiving chamber. Depressing the plunger will infuse a substance through the first needle while simultaneously withdrawing a substance through the second needle. Reverse action is possible.

9 Claims, 2 Drawing Sheets

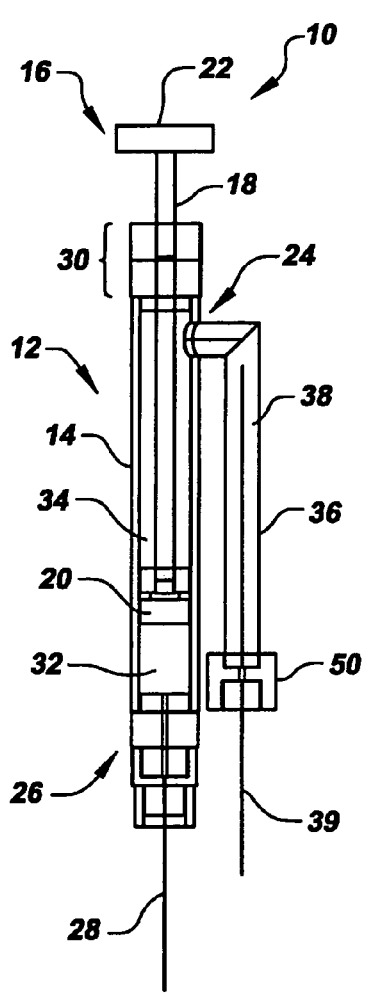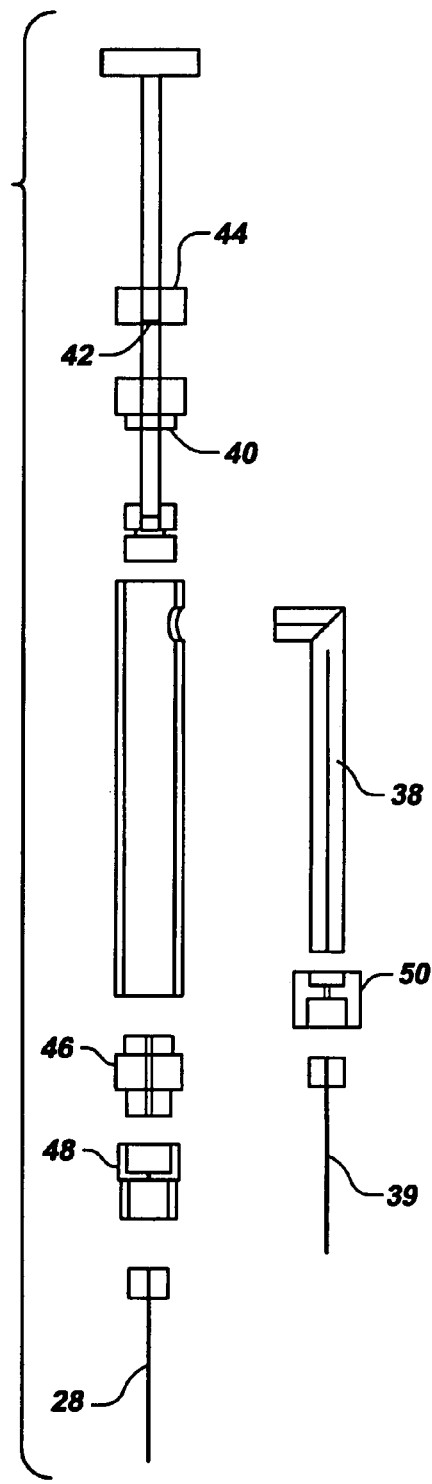

SYRINGE DEVICE FOR SIMULTANEOUS INFUSION AND WITHDRAWAL

BACKGROUND OF THE INVENTION

This invention relates generally to syringe devices and more particularly, but without limitation thereto, to a multiple needled syringe device that permits a simultaneous infusion and withdrawal of one or more substances through a single action.

The prior art contains a variety of devices wherein it is known to use dual needles with either a single or multiple chambered device so as to dispense one or more substances simultaneously through the hollow needles. U.S. Pat. Nos. 4,150,669 and 6,065,371 are illustrative of such designs.

There are however circumstances where it is desirable to inject a substance into an environment while simultaneously permitting a withdrawal of a substance from the environment. Such a scenario exists, for example, in the testing of substances known to pose considerable adverse health effects to human beings and perhaps other life forms. Two such substances may be chemical or biological hazards, wherein leakage of only a very minute amount can wreak deadly havoc.

In laboratory testing or other use of such substances, the substances themselves may be housed within a glass vial having a self-sealing lid or septum over the open end of the glass container. The lid is designed to permit perforation by, for example, a hypodermic needle so that substances can be injected and withdrawn through the safety of the self-sealing lid.

In the aforementioned chemical and biological hazard research field, it has been learned that injection into a vial containing such hazards can produce an undesirable increase in pressure or volume within the vial.

To offset this undesirable pressure or volume increase, injection and withdrawal from the vial has been performed through the use of two separate syringes used at the same time. Such a technique has produced several negative consequences. For one, several syringes are contaminated in the process. In addition, it is challenging to produce substantially equal infusion and withdrawal during this process.

As a consequence, there is a need in the art for a single syringe device that permits simultaneous infusion and withdrawal while preferably being performed via a single action.

SUMMARY OF THE INVENTION

The invention answers the aforementioned needs. The invention includes a syringe having a barrel and a plunger disposed to be capable of sliding back and forth longitudinally within the barrel. The plunger includes a shaft and a plunger head, the latter providing a seal between an actuation end of the barrel and an administering end of the barrel. A hollow needle is sealed to the administering end of the barrel.

As in traditional syringe design, a chamber is defined by the syringe barrel, the plunger head and the hollow needle sealed to the administering end of the barrel. This needle of course provides fluid communication between the chamber and an environment outside of the chamber.

In a departure from traditional syringe design, a second chamber is located near the actuation end of the barrel. The second chamber is defined by the syringe cylindrical barrel, the plunger head and a seal that seals around the plunger shaft and the actuation end of the barrel.

A receiving container having a second hollow needle is attached and sealed to the syringe, to thereby define a receiving chamber that is arranged to be in fluid communication with the second chamber of the syringe and, via the second hollow needle, to be in fluid communication with an environment outside of said receiving chamber.

The hollow needles are preferably arranged in parallel and oriented to perforate in the same direction. Once perforation of a septum, for example, is performed, depressing the plunger will infuse a substance into the volume of an associated vial while simultaneously withdrawing from the volume of the vial. The step of infusion and withdrawal occurs with a single action, and can operate in reverse by drawing the plunger in an opposite direction.

Other objects, advantages and new features of the invention will become apparent from the following detailed description of the invention when considered in conjunction with the accompanied drawings.

BRIEF DESCRIPTION OF THE DRAWINGS

FIG. 1 illustrates an assembled view of one embodiment of the invention.

FIG. 2 is an exploded view of the embodiment of the invention shown in FIG. 1.

DESCRIPTION OF THE INVENTION

Figure 3:
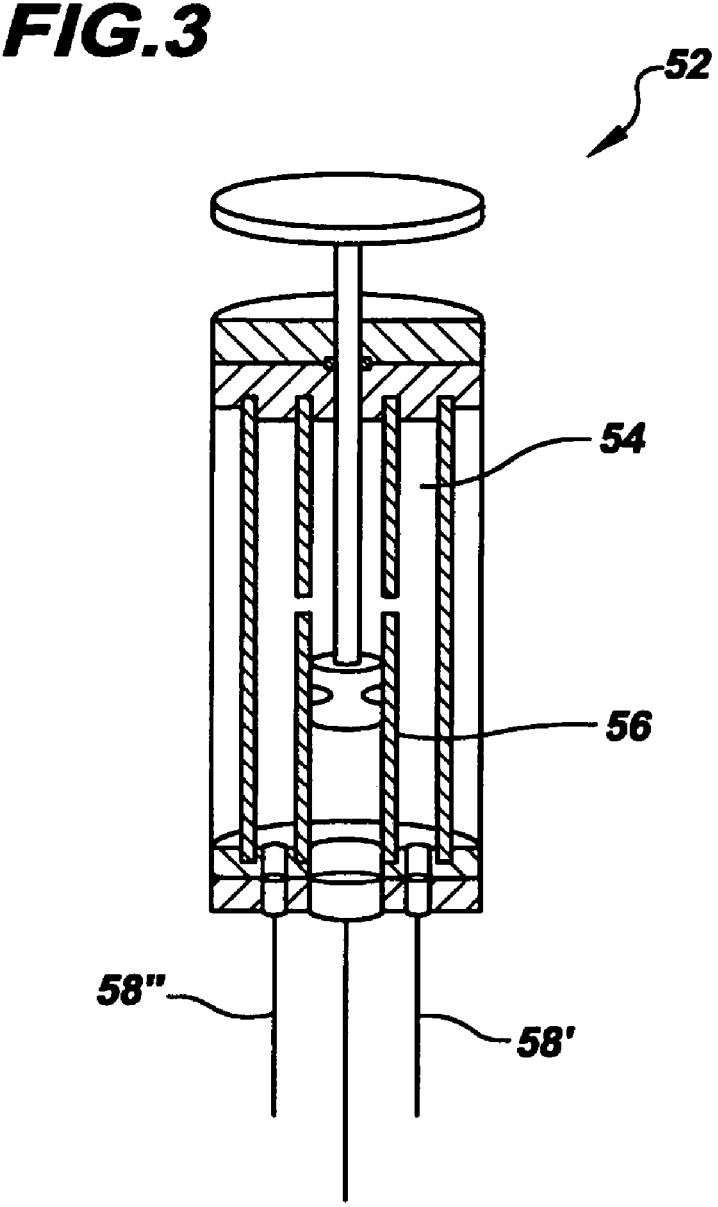
FIG. 3 illustrates an alternative embodiment of the invention.

Referring to FIG. 1, a syringe device 10 is shown having the capability of infusing and withdrawing one or more substances simultaneously. Device 10 includes a syringe 12 that is made primarily of a barrel 14, in this example shown to be of a circular cross-section. Within the barrel is a plunger 16 that includes a shaft 18 and a plunger head 20 that fits in a sealing relationship with the interior walls of barrel 14. In a conventional way, plunger 16 and plunger head 20 are designed to be capable of reciprocating the longitudinal dimension of barrel 14, and may be fitted with a suitable head piece 22 for the application of finger or machine actuated pressure or tension. Syringe 12 is shown with an actuation end 24 and an administering end 26.

As can be seen there is a needle (hollow) 28 that is suitably attached and sealed to administering end 26 of barrel 14. In the vicinity of actuation end 24 of barrel 14, there is a shaft sealing cap shown generally at 30 that seals this end of the barrel. As will be described further, cap 30 is sealed both to barrel 14 as well as to plunger shaft 18. The sealing relationship between shaft 18 and cap 30 allows the shaft to move longitudinally with respect to barrel 14 while still maintaining a suitable seal.

As can be seen in FIG. 1, a first chamber 32 is defined by barrel 14, plunger head 20 and hollow needle 28. Also created is a second chamber 34 being defined by barrel 14, plunger head 20 and shaft sealing cap 30. As is apparent, hollow needle 28 permits fluid communication between first chamber 32 and an environment outside of this chamber. In utilization, this environment may be that contained within a sealed vial, as previously explained.

As is also shown in FIG. 1, a receiving container 36 is illustrated. Receiving container 36 lies exteriorly adjacent to barrel 14 and defines a receiving chamber 38 that, by virtue of a suitable attachment to syringe 12, is in fluid communication with second chamber 34 of syringe 12. A second hollow needle 39 is suitably sealed to one end of receiving container 36 to provide a fluid communication between chamber 38 and an environment outside of this chamber. As with syringe 12, this environment may be that of a sealed vial, as earlier referenced.

For ease of usage, needles 28 and 39 are arranged to be substantially parallel and further are oriented to perforate in the same direction. Staggering of these needle may be preferred to aid in the initial perforation of a self-sealing septum attached to a specimen vial.

FIG. 2 shows an explosive view of the embodiment illustrated in FIG. 1. Shaft sealing cap 30 is portrayed of three parts, barrel cap 40, "O" ring 42 and "O" ring seal cap 44. The particulars of this arrangement are not intended to present the only way in which the sealing of actuation end 24 of barrel may be performed. The essence of shaft seal cap 30 is that a seal be provided both to the actuation end of barrel 14 as well as to the shaft of plunger 16.

Similarly, hollow needle 28 is sealed and attached to actuation end 26 of barrel by a barrel cap 46 and a transition element 48. Those skilled in this art will realize that a myriad of mechanisms may be used to seal hollow needle 28 to barrel 14. It is of course within these schemes to provide for the utilization of typical hypodermic needles and therefore ways of mating such needles will be readily realized.

As with first hollow needle 28, second hollow needle 39 is similarly attached and sealed to receiving container 38 via a suitable transition element 50.

In operation, as plunger 16 moves towards actuation end 26 of syringe 12, the volume in first chamber 32 is reduced while at the same time the volume in second chamber 34 is increased. As the volume in chamber 32 is decreased, the pressure in this chamber is increased. This pressure increase is what drives a substance within the first chamber from the chamber. As plunger 16 is advanced towards administering end 26 of syringe 12, the volume in second chamber 34 is increased, resulting in a pressure drop in this chamber. This pressure drop permits the reception of a substance through needle 39 and into at least receiving chamber 38 of receiving container 36.

As previously explained, the actuation of the device may also be conducted in as reverse fashion to that described, wherein a substance is expelled from chamber 38 and drawn into chamber 32. Such reverse flow will occur when plunger 16 is moved towards actuation end 24 of syringe 12.

Referring now to FIG. 3, an alternative syringe device 52 is shown in a partial cross-section. In this embodiment, a receiving chamber 54 is shown to substantially surround barrel 56 of syringe 52. Two hollow needles 58' and 58" are shown as utilized with receiving chamber 54, though one or other multiples of needles can be visualized by one skilled in the art. Furthermore, though receiving chamber 54 is shown to be somewhat coaxial with that of barrel 56 of this embodiment, it will be realized that receiving chamber 54 could still substantially surround barrel 56 but have a longitudinal axis that is offset from that of barrel 56.

Those skilled in the art will realize that within the scope of the invention one may also use multiple hollow needles wherein one needle lies inside of, and is substantially coaxial with, a second hollow needle. In such an arrangement, a substance is infused via the inner needle and withdrawn via the outer needle, or vice-versa.

In all embodiments of the invention, well known manufacturing techniques will enable the hollow needles utilized to be very closely spaced, enhancing their applicability to a wide variety of self-sealing septa.

Obviously, many modifications and variations of the invention are possible in light of the above description. It is therefore to be understood that within the scope of the claims, the invention may be practiced otherwise than as has been specifically described.

What is claimed is:

1. An apparatus comprising:
  a syringe including
    a cylindrical barrel;
    a plunger including a shaft and a plunger head disposed within said cylindrical barrel to reciprocate longitudinally within said cylindrical barrel, said plunger head providing a seal between an actuation end of said cylindrical barrel and an administering end of said cylindrical barrel;
    a first hollow needle;
    a first chamber defined by said cylindrical barrel, said plunger head, and said first hollow needle sealed to said administering end of said cylindrical barrel, said first hollow needle providing fluid communication between said first chamber and an environment outside of said first chamber;
    a second chamber defined by said cylindrical barrel, said plunger head, and a shaft seal sealed to said plunger shaft and to said actuation end of said cylindrical barrel;
  a second hollow needle; and
  a receiving container defining a receiving chamber, said receiving container sealed to said syringe and to said second hollow needle so that said receiving chamber is in fluid communication with said second chamber of said syringe and said second hollow needle provides fluid communication between said receiving chamber and an environment outside of said receiving chamber.

2. The apparatus of claim 1 wherein said receiving container includes a cylindrical housing.

3. The apparatus of claim 2 wherein said cylindrical housing of said receiving container is substantially parallel to said cylindrical barrel of said syringe.

4. The apparatus of claim 3 wherein said cylindrical housing of said receiving chamber is disposed exteriorly adjacent said cylindrical barrel of said syringe.

5. The apparatus of claim 3 wherein said cylindrical housing of said receiving chamber substantially surrounds said cylindrical barrel of said syringe.

6. The apparatus of claim 1 wherein said first and second hollow needles are disposed to be substantially parallel and wherein said needles are arranged to perforate in the same direction.

7. The apparatus of claim 6 wherein said needles are staggered with respect to each other.

8. An apparatus comprising:
  a syringe including
    a cylindrical barrel;
    a plunger including a shaft and a plunger head disposed within said cylindrical barrel to reciprocate longitudinally within said cylindrical barrel, said plunger head providing a seal between an actuation end of said cylindrical barrel and an administering end of said cylindrical barrel;
    a first hollow needle;
    a first chamber defined by said cylindrical barrel, said plunger head, and said first hollow needle sealed to said administering end of said cylindrical barrel, said first hollow needle providing a fluid communication between said first chamber and an environment outside of said first chamber;

a second chamber defined by said cylindrical barrel, said plunger head, and a shaft seal sealed to said plunger shaft and to said actuation end of said cylindrical barrel;

a second hollow needle, wherein said first and second hollow needles are disposed to be substantially parallel to each other and wherein said needles are arranged to perforate in the same direction;

a receiving container defining a receiving chamber, said receiving container sealed to said syringe and to said second hollow needle so that said receiving chamber is in fluid communication with said second chamber of said syringe and said second hollow needle provides fluid communication between said receiving chamber and an environment outside of said receiving chamber, wherein said receiving container includes a second cylindrical barrel disposed to be substantially parallel to and exteriorly adjacent of said cylindrical barrel of said syringe.

9. The apparatus of claim 8 wherein said first and second hollow needles are staggered with respect to each other.

* * * * *